United States Patent [19]

Satoh et al.

[11] Patent Number: 4,469,704
[45] Date of Patent: Sep. 4, 1984

[54] 2,3-BUTANEDIOL DIESTER DERIVATIVES, PROCESS FOR PRODUCING THE SAME, AND AN ANTIULCER DRUG CONTAINING THE SAME

[75] Inventors: Susumu Satoh, Chiba; Kinichi Mogi, Abiko; Saburo Murakami, Chiba; Toshiaki Nakashima, Shisui, all of Japan

[73] Assignee: SS Pharmaceutical Co., Ltd., Tokyo, Japan

[21] Appl. No.: 333,772

[22] Filed: Dec. 23, 1981

[30] Foreign Application Priority Data

Dec. 26, 1980 [JP] Japan .................................. 55-186144
Jun. 4, 1981 [JP] Japan .................................. 56-86034
Jul. 14, 1981 [JP] Japan .................................. 56-109778
Oct. 2, 1981 [JP] Japan .................................. 56-157110

[51] Int. Cl.³ .................... A01N 37/02; A01N 37/06; A01K 31/23
[52] U.S. Cl. .................... 424/312; 424/314; 260/410; 260/410.9 R; 260/413
[58] Field of Search .................... 260/410.9 D, 410 R, 260/413 R, 413 K, 413 L; 424/312, 314

[56] References Cited

U.S. PATENT DOCUMENTS

| | | | |
|---|---|---|---|
| 2,357,077 | 8/1944 | Brown | 260/410 R |
| 3,156,612 | 11/1964 | Butler et al. | 424/314 |
| 3,329,826 | 7/1967 | Pine et al. | 260/410.9 D X |
| 3,671,654 | 6/1972 | Nosler et al. | 424/312 |
| 3,833,624 | 9/1974 | Bork | 260/410 R X |
| 3,928,557 | 12/1975 | Wright et al. | 424/312 X |
| 3,970,759 | 7/1976 | Frankenfeld et al. | 424/312 |
| 4,025,645 | 5/1977 | Jelenko | 424/312 |
| 4,272,548 | 6/1981 | Gatzen et al. | 424/312 |

OTHER PUBLICATIONS

Shanzer, Tetrahedron Letters, vol. 21, pp. 221–222, (1980).

Primary Examiner—Helen M. S. Sneed
Attorney, Agent, or Firm—Oblon, Fisher, Spivak, McClelland & Maier

[57] ABSTRACT

The specification describes as antiulcer drug containing as an active ingredient a 2,3-butanediol diester derivative represented by the formula (I):

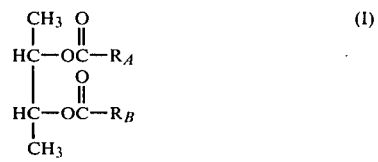

where $R_A$ may for example be a saturated or unsaturated alkyl or phenyl styryl group and $R_B$ may for example be a saturated or unsaturated alkyl, phenyl, phenylalkyl, phenylpropenyl or phenoxyalkyl group. These groups may optionally be substituted. Many of 2,3-butanediol diester derivatives embraced by the formula (I) are novel. Also described are a novel process for preparing such novel 2,3-butanediol diester derivatives. The 2,3-butandiol diester derivatives of the formula (I) has an action to depress strongly the growth of peptic ulcer and has a very low toxicity.

8 Claims, No Drawings ized with lower alkyl group, lower alkoxy group or halogen atom, phenyl alkyl group, phenyl propenyl group, phenyloxy alkyl group, or a group represented by the phenyl group of the present invention to provide an antiulcer drug containing a butanediol diester represented by the formula (I).

2,3-BUTANEDIOL DIESTER DERIVATIVES, PROCESS FOR PRODUCING THE SAME, AND AN ANTIULCER DRUG CONTAINING THE SAME

BACKGROUND OF THE INVENTION (1) Field of the Invention

The present invention relates to 2,3-butanediol diester derivatives, process for producing the same, and an antiulcer drug containing the same.

(2) Description of the Prior Art

Heretofore, it has been known that coixenolide, a constituent of coix seed, has an antitumor effect (Japanese Patent Publication No. 36-13349) and some 2,3-butanediol diesters can be used as a durable perfume/flavor agent or modifier (Japanese Patent Laid-open No. 55-154940).

SUMMARY OF THE INVENTION

The present inventors have carried out a series of researches on the pharmacological actions of 2,3-butanediol diester derivatives (abbreviated as "butanediol diester" hereunder), and as the result of these researches, they have discovered that the butanediol diester represented by the formula (I)

$$\begin{array}{c} CH_3 \ O \\ | \quad \| \\ HC-OC-R_A \\ | \quad O \\ | \quad \| \\ HC-OC-R_B \\ | \\ CH_3 \end{array} \quad (I)$$

where $R_A$ is a saturated or unsaturated alkyl group which may have a branched chain, or a group represented by

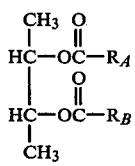

(where $R_1$ is a hydrogen atom, cyano group, or lower alkyl group, and $R_2$ is a hydrogen atom, halogen atom, lower alkyl group, lower alkyloxy group, or lower acyloxy group); $R_B$ is a saturated or unsaturated alkyl group which may have a branched chain, phenyl group which may be substituted with lower alkyl group, lower alkoxy group or halogen atom, phenyl alkyl group, phenyl propenyl group, phenyloxy alkyl group, or a group represented by

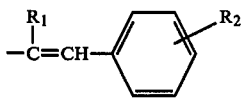

(where $R_3$ is a hydrogen atom, halogen atom, cyano group, lower alkyl group, or phenyl group, and $R_4$ is a hydrogen atom, lower alkyl group, or phenyl group, and $R_5$ is a phenyl group which may be substituted with lower alkyl group, lower alkoxy group, acyloxy group or halogen atom). has an action to depress strongly the growth of peptic ulcer and has a very low toxicity and that among the compounds represented by the formula (I) the compound represented by the following formula (II) is a novel compound:

$$\begin{array}{c} CH_3 \ O \\ | \quad \| \\ HC-OC-R_A \\ | \quad O \\ | \quad \| \\ HC \quad OC-R_{B'} \\ | \\ CH_3 \end{array} \quad (II)$$

where $R_A$ is as defined above, $R_{B'}$ is a phenyl group which may be substituted with lower alkyl group, lower alkoxy group or halogen atom, phenyl alkyl group, phenyl propenyl group, phenyloxy alkyl group, or a group represented by

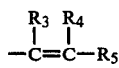

(where $R_3$ is a hydrogen atom, halogen atom, cyano group, lower alkyl group, or phenyl group, and $R_4$ is a hydrogen atom, lower alkyl group, or phenyl group, and $R_5$ is a phenyl group which may be substituted with lower alkyl group, lower alkoxy group, acyloxy group or halogen atom).

Therefore, it is an object of the present invention to provide an antiulcer drug containing a butanediol diester represented by the formula (I).

It is another object of the present invention to provide a novel butanediol diester represented by the formula (II).

It is a further object of the present invention to provide a process for producing the butanediol diester represented by the formula (II).

DESCRIPTION OF THE INVENTION AND PREFERRED EMBODIMENTS

The butanediol diester (I) of this invention is a known compound or a novel compound produced by a process based on known reaction or any one of the following processes.

Process for production:

(1) According to this process, 2,3-butanediol (III) is converted to a 2,3-butanediol monoester derivative (V) by the reaction with a carboxylic acid (IV) or an active derivative thereof, and (V) is converted to the object compound (I) by the reaction with a carboxylic acid (VI) or an active derivative.

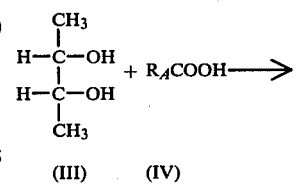

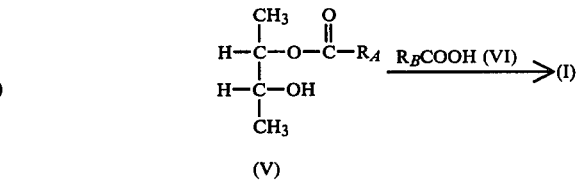

where $R_A$ and $R_B$ are as defined above.

(2) According to this process, 2,3-butanediol (III) is converted to a 2,3-butanediol monoester derivative (VII) by the reaction with a carboxylic acid (VI) or an active derivative thereof, and (VII) is converted to the object compound (I) by the reaction with a carboxylic acid (IV).

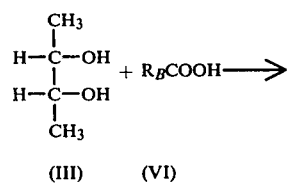

(III)    (VI)

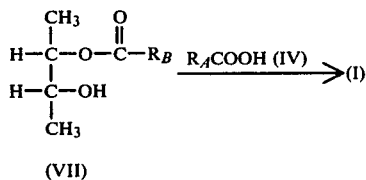

(VII)

where $R_A$ and $R_B$ are as defined above.

(3) According to this process, 2,3-butanediol (III) is converted to a 2,3-butanediol diester derivative (I') by the reaction with a carboxylic acid (IV) or an active derivative thereof in twofold moles.

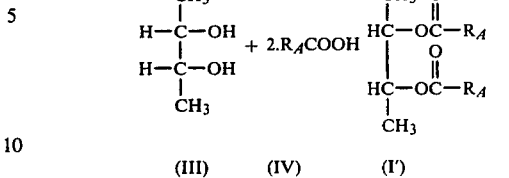

(III)         (IV)         (I')

where $R_A$ is as defined above.

Examples of the active derivatives of the carboxylic acids (IV) and (VI) used in these processes include acid halogenide, acid anhydride, and mixed acid anhydrides. If these compounds are to be used, the reaction should preferably be carried out in the presence of a deacidifier such as pyridine, tertiary amine, alkali carbonate, alkali hydroxide, and hydrogenated alkali.

Typical butanediol diesters produced by the above processes are shown in Table 1, in which compounds No. 1 to 21 are known and compounds No. 22 to 81 are novel.

| Compound No. | $R_A$ | $R_B$ | $n_D^{20}$ | Melting point °C. | NMR (δppm: CCl$_4$) |
|---|---|---|---|---|---|
| 1 | (CH$_2$)$_6$CH$_3$ | (CH$_2$)$_6$CH$_3$ | 1.436 | | 4.7~5.2(m.2H) 2.3(t.4H) 1.1~1.9(m.26H) 0.9(t.6H) |
| 2 | (CH$_2$)$_7$CH$_3$ | (CH$_2$)$_7$CH$_3$ | 1.439 | | 4.7~5.1(m.2H) 2.2(t.4H) 1.1~1.9(m.30H) 0.9(t.6H) |
| 3 | (CH$_2$)$_8$CH$_3$ | (CH$_2$)$_8$CH$_3$ | 1.444 | | 4.7~5.2(m.2H) 2.2(t.4H) 1.1~1.9(m.34H) 0.9(t.6H) |
| 4 | (CH$_2$)$_9$CH$_3$ | (CH$_2$)$_9$CH$_3$ | 1.445 | | 4.6~5.2(m.2H) 2.2(t.4H) 1.1~1.9(m.38H) 0.9(t.6H) |
| 5 | (CH$_2$)$_{10}$CH$_3$ | (CH$_2$)$_{10}$CH$_3$ | | 40~42 | 4.7~5.2(m.2H) 2.3(t.4H) 1.1~1.9(m.42H) 0.9(t.6H) |
| 6 | (CH$_2$)$_{12}$CH$_3$ | (CH$_2$)$_{12}$CH$_3$ | | 51~53 | 4.7~5.2(m.2H) 2.3(t.4H) 1.1~1.9(m.50H) 0.9(t.6H) |
| 7 | (CH$_2$)$_{14}$CH$_3$ | (CH$_2$)$_{14}$CH$_3$ | | 55~57 | 4.7~5.2(m.2H) 2.3(t.4H) 1.1~1.8(m.58H) 0.9(t.6H) |
| 8 | CH$_3$–CHCH$_2$CH$_3$ | CH$_3$–CHCH$_2$CH$_3$ | 1.426 | | 4.6~5.2(m.2H) 2.0~2.6(m.2H) 1.0~2.0 (m.16H) 0.9(t.6H) |
| 9 | CH$_3$–CHCH$_2$CH$_2$CH$_3$ | CH$_3$–CHCH$_2$CH$_2$CH$_3$ | 1.429 | | 4.7~5.2(m.2H) 2.1~2.7(m.2H) 1.1(d.6H) 0.7~1.8(m.20H) |
| 10 | CH$_3$ CH$_2$CHCH$_2$CH$_3$ | CH$_3$ CH$_2$CHCH$_2$CH$_3$ | 1.433 | | 4.7~5.2(m.2H) 2.1~2.4(m.4H) 1.6~2.1(m.2H) 1.1~1.5(m.4H) 1.2(d.6H) 0.95(d.6H) 0.9(t.6H) |
| 11 | CH$_3$ CH$_2$CH$_2$CHCH$_3$ | CH$_3$ CH$_2$CH$_2$CHCH$_3$ | 1.432 | | 4.7~5.2(m.2H) 2.4(t.4H) 1.5(m.6H) 1.2(d.6H) 0.9(d.12H) |
| 12 | CH$_3$ CH$_3$ CH$_3$CHCH$_2$C–CH$_3$ CH$_3$ | CH$_3$ CH$_3$ CH$_3$CHCH$_2$C–CH$_3$ CH$_3$ | 1.437 | | 4.6~5.1(m.2H) 1.8~2.4(m.6H) 0.8–1.5 (m.16H) 0.9(s.18H) |
| 13 | CH$_2$CH$_2$CH=CH$_2$ | —CH$_2$CH$_2$CH=CH$_2$ | 1.446 | | 5.4~6.1(m.2H) 4.6~5.2(m.3H) 2.3(m.8H) 1.1(d.6H) |
| 14 | CH=CH(CH$_2$)$_6$CH$_3$ | —CH=CH(CH$_2$)$_6$CH$_3$ | 1.464 | | 6.5~7.1(m.2H) 5.7(d.2H) 4.7~5.2(m.2H) 1.9~2.5(m.4H) 1.0–1.9(m.26H) 0.9(t.6H) |
| 15 | (CH$_2$)$_7$CH=CHCH$_2$– —CH=CH(CH$_2$)$_4$CH$_3$ | —(CH$_2$)$_7$CH=CHCH$_2$– —CH=CH(CH$_2$)$_4$CH$_3$ | 1.471 | | 5.1~5.5(m.8H) 4.6~5.1(m.2H) 2.6~3.0 (m.4H) 0.8~2.5(m.56H) |
| 16 | (CH$_2$)$_6$CH$_2$– —(CH=CHCH$_2$)$_3$CH$_3$ | —(CH$_2$)$_6$CH$_2$– —(CH=CHCH$_2$)$_3$CH$_3$ | 1.481 | | 5.0~5.5(m.12H) 4.5~5.1(m.2H) 2.5~3.0 (m.8H) 0.8~2.5(m.44H) |
| 17 | (CH$_2$)$_9$CH$_3$ | —(CH$_2$)$_4$CH$_3$ | 1.440 | | 4.7~5.1(m.2H) 2.3(t.4H) 1.1~1.9(m.28H) 0.9(t.6H) |
| 18 | '' | —(CH$_2$)$_6$CH$_3$ | 1.443 | | 4.7~5.1(m.2H) 2.2(t.4H) 1.1~2.0(m.30H) 0.9(t.6H) |
| 19 | '' | —(CH$_2$)$_8$CH$_3$ | 1.445 | | 4.7~5.1(m.2H) 2.2(t.4H) 1.1~2.0(m.32H) 0.9(t.6H) |
| 20 | '' | —CH=CHCH$_8$ | 1.450 | | 6.5~7.1(m.1H) 5.75(m.1H) 4.7~5.1(m.2H) 2.2 |

-continued

| Compound No. | $R_A$ | $R_B$ | $n_D^{20}$ | Melting point °C. | NMR (δppm: CCl₄) |
|---|---|---|---|---|---|
| 21 | " | trans —(CH₂)₇CH=CH(CH₂)₇ cis-CH₃ | 1.456 | | (t.2H) 1.9(dd.3H) 1.1~1.8(m.22H) 0.9(t.3H) 5.0~5.5(m.2H) 4.6~5.0(m.2H) 1.1~2.4 (m.52H) 0.9(t.6H) |
| 22 | —(CH₂)₄CH₃ | —CH=CH— ⌬ | 1.514 | | 7.6(d.1H) 7.2~7.6(m.5H) 6.3(d.1H) 4.7~5.3(m.2H) 2.25(t.2H) 1.0~1.9(m.12H) 0.9(t.3H) |
| 23 | —(CH₂)₆CH₃ | " | 1.509 | | 7.6(d.1H) 7.2~7.5(m.5H) 6.3(d.1H) 4.7~5.3(m.2H) 2.25(t.2H) 1.0~1.9(m.16H) 0.9(t.3H) |
| 24 | —(CH₂)₇CH₃ | " | 1.505 | | 7.6(d.1H) 7.2~7.5(m.5H) 6.3(d.1H) 4.7~5.3(m.2H) 2.25(t.2H) 1.0~1.9(m.18H) 0.9(t.3H) |
| 25 | —(CH₂)₈CH₃ | " | 1.501 | | 7.7(d.1H) 7.3~7.7(m.5H) 6.4(d.1H) 4.8~5.7(m.2H) 2.0~2.5(t.2H) 1.0~1.8(m.20H) 0.9(t.3H) |
| 26 | —(CH₂)₉CH₃ | " | 1.503 | | 7.6(d.1H) 7.2~7.5(m.5H) 6.3(d.1H) 4.7~5.2(m.2H) 2.2(t.2H) 1.0~1.8(m.22H) 0.9(t.3H) |
| 27 | —(CH₂)₁₀CH₃ | " | 1.500 | | 7.6(d.1H) 7.1~7.5(m.5H) 6.3(d.1H) 4.7~5.2(m.2H) 2.2(t.2H) 1.0~1.8(m.24H) 0.9(t3H) |
| 28 | —(CH₂)₈CH=CH₂ | " | 1.509 | | 7.6(d.1H) 7.3(m.5H) 6.35(d.1H) 5.4~6.1(m.1H) 4.7~5.3(m.4H) 2.2(t.2H) 1.0~2.1(m.20H) |
| 29 | —(CH₂)₇CH=CH(CH₂)₇CH₃ (cis) | " | 1.503 | | 7.6(d.1H) 7.1~7.5(m.5H) 6.8(d.1H) 5.1~5.4(m.2H) 4.8~5.1(m.2H) 1.0~2.4(m.34H) 0.9(t.3H) |
| 30 | —(CH₂)₇CH=CH(CH₂)₇CH₃ (trans) | " | 1.505 | | 7.65(d.1H) 7.2~7.5(m.5H) 6.35(d.1H) 5.2~5.5(m.2H) 4.9~5.2(m.2H) 1.1~2.5(m.34H) 0.9(t.3H) |
| 31 | —(CH₂)₄CH₃ | —CH=CH— ⌬CH₃ | 1.504 | | 7.55(d.1H) 7.3(d.1H) 7.05(d.2H) 6.3(d.1H) 4.7~5.2(m.1H) 2.3(s.3H) 2.0~2.4(t.2H) 1.0~2.0(m.12H) 0.9(t.3H) |
| 32 | —(CH₂)₉CH₃ | " | 1.499 | | 7.5(d.1H) 7.35(d.2H) 7.05(d.2H) 6.25(d.1H) 4.7~5.3(m.2H) 2.35(s.3H) 2.2(t.2H) 1.1~1.9(m.22H) 0.9(t.3H) |
| 33 | " | " | | 72~74 | 7.5(d.2H) 7.35(d.4H) 7.15(d.4H) 6.35(d.2H) 4.7~5.1(m.2H) 2.3(s.6H) 1.4(d.6H) |
| 34 | —(CH₂)₄CH₃ | —CH=CH— ⌬OCH₃ | 1.528 | | 7.5(d.1H) 7.4(d.2H) 6.8(d.2H) 6.15(d.1H) 4.7~5.3(m.2H) 3.8(s.2H) 2.2(t.2H) 1.0~1.9(m.12H) 0.9(t.3H) |
| 35 | —(CH₂)₉CH₃ | " | 1.519 | | 7.5(d.1H) 7.4(d.2H) 6.8(d.2H) 6.15(d.1H) 4.7~5.2(m.2H) 3.8(s.3H) 2.2(t.2H) 1.0~1.9(m.22H) 0.9(t.3H) |

-continued

| Compound No. | R_A | R_B | $n_D^{20}$ | Melting point °C. | NMR (δppm: CCl_4) |
|---|---|---|---|---|---|
| 36 | ![4-methoxyphenyl-CH=CH-] -CH=CH-C_6H_4-OCH_3 | " | | 115~117 | 7.6(d.2H) 7.4(d.2H) 7.3(d.2H) 6.3(d.2H) 4.9~5.4(m.2H) 3.8(s.6H) 1.4(d.6H) |
| 37 | -(CH_2)_4CH_3 | -CH=CH-C_6H_4-Cl | 1.524 | | 7.6(d.1H) 7.4(d.d.4H) 6.35(d.1H) 4.8~5.4(m.2H) 2.3(t.3H) 1.1~1.9(m.12H) 0.9(t.3H) |
| 38 | -(CH_2)_9CH_3 | " | 1.514 | | 7.6(d.1H) 7.4(d.d.4H) 6.35(d.1H) 4.8~5.4(m.2H) 2.3(t.3H) 1.1~1.9(m.22H) 0.9(t.3H) |
| 39 | -CH=CH-C_6H_4-Cl | " | | 133~136 | 7.6(d.2H) 7.3(m.8H) 6.3(d.2H) 4.9~5.4(m.2H) 1.3(d.6H) |
| 40 | -(CH_2)_9CH_3 | -CH=CH-C_6H_2(OCH_3)_3 | 1.520 | | 7.45(d.1H) 6.65(s.2H) 6.2(d.1H) 4.8~5.3(m.2H) 3.78(d.9H) 2.2(t.2H) 1.0~1.9(m.22H) 0.9(t.3H) |
| 41 | " | -CH=CH-C_6H_4-OCOCH_3 | 1.507 | | 7.55(d.1H) 7.5(d.2H) 7.05(d.2H) 6.3(d.1H) 4.7~5.2(m.2H) 2.25(s.3H) 2.2(t.2H) 1.1~2.0(m.22H) 0.9(t.3H) |
| 42 | -CH=CH-C_6H_4-OCOCH_3 | " | | 112~116 | 7.6(d.2H) 7.45(d.4H) 7.05(d.4H) 6.3(d.2H) 5.0~5.4(m.2H) 2.3(s.6H) 1.35(d.6H) |
| 43 | -C(CN)=CH-C_6H_5 | -C(CN)=CH-C_6H_5 | | 177~180 | 8.25(s.2H) 7.8~8.1(m.4H) 7.3~7.7(m.6H) 5.1~5.5(m.2H) 1.4(d.6H) |
| 44 | -(CH_2)_4CH_3 | " | 1.523 | | 8.15(s.1H) 7.7~8.1(m.2H) 7.2~7.7(m.3H) 4.7~5.4(m.2H) 2.25(t.2H) 1.0~1.9(m.12H) 0.9(t.3H) |

-continued

| Compound No. | $R_A$ | $R_B$ | $n_D^{20}$ | Melting point °C. | NMR (δppm: CCl₄) |
|---|---|---|---|---|---|
| 45 | —(CH₂)₆CH₃ | " | 1.509 | | 8.15(s.1H) 7.7~7.8(m.2H) 7.3~7.7(m.3H) 4.8~5.3(m.2H) 2.25(t.2H) 1.0~2.0(m.16H) 0.9(t.3H) |
| 46 | —(CH₂)₇CH₃ | " | 1.516 | | 8.2(s.1H) 7.8~8.1(m.2H) 7.3~7.7(m.3H) 4.7~5.3(m.2H) 2.3(t.2H) 1.0~1.8(m.18H) 0.9(t.3H) |
| 47 | —(CH₂)₈CH₃ | 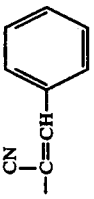 $\underset{CN}{\underset{|}{-C}}=CH$ | 1.514 | | 8.15(s.1H) 7.7~8.1(m.2H) 7.2~7.7(m.3H) 4.7~5.4(m.2H) 2.25(t.2H) 1.0~1.9(m.20H) 0.9(t.3H) |
| 48 | —(CH₂)₉CH₃ | " | 1.514 | | 8.13(s.1H) 7.7~8.1(m.2H) 7.3~7.7(m.3H) 4.8~5.3(m.2H) 2.0~2.5(t.2H) 1.0~1.9(m.22H) 0.9(t.3H) |
| 49 | —(CH₂)₁₀CH₃ | " | 1.512 | | 8.1(s.1H) 7.8~8.1(m.2H) 7.3~7.6(m.3H) 4.8~5.4(m.2H) 2.3(t.2H) 1.1~1.7(m.24H) 0.9(t.3H) |
| 50 | —CH=CHCH₃ | " | | 78~81 | 8.1(s.1H) 7.7~8.1(m.2H) 7.3~7.6(m.3H) 6.6~7.1(m.1H) 5.6~6.0(m.1H) 4.7~5.3(m.2H) 1.85(d.d.3H) 1.30(d.3H) 1.25(d.3H) |
| 51 | $\underset{CH_3}{\underset{|}{-C}}=CHCH_3$ | " | 1.550 | | 8.1(s.1H) 7.7~8.1(m.1H) 7.3~7.6(m.3H) 6.5~7.0(m.1H) 4.8~5.4(m.2H) 1.8(s.3H) 1.75(d.3H) 1.35(d.3H) 1.3(d.3H) |
| 52 | —(CH₂)₇CH=CH(CH₂)₇CH₃ (cis) | " | 1.509 | | 8.1(s.1H) 7.7~8.0(m.2H) 7.2~7.6(m.3H) 4.7~5.4(m.4H) 1.0~2.4(m.34H) 0.9(t.3H) |
| 53 | —(CH₂)₇CH=CH(CH₂)₇CH₃ (Trans) | " | 1.506 | | 8.1(s.1H) 7.7~8.0(m.2H) 7.2~7.6(m.3H) 4.7~5.4(m.4H) 1.0~2.4(m.34H) 0.9(t.3H) |
| 54 | —(CH₂)₄CH₃ | 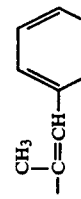 $\underset{CH_3}{\underset{|}{-C}}=CH$ | 1.501 | | 7.6(m.1H) 7.3(b.s.5H) 4.8~5.3(m.2H) 2.25(t.2H) 2.1(d.3H) 1.1~2.0(m.22H) 0.9(t.3H) |
| 55 | —(CH₂)₉CH₃ | " | 1.501 | | 7.6(m.1H) 7.34(b.s.5H) 4.8~5.3(m.2H) 2.25(t.2H) 2.1(d.3H) 1.1~2.0(m.22H) 0.9(t.3H) |
| 56 | —(CH₂)₁₀CH₃ | " | 1.500 | | 7.6(m.1H) 7.3(b.s.5H) 4.8~5.3(m.2H) 2.25(t.2H) 2.1(d.3H) 1.0~2.0(m.24H) 0.9(t.3H) |
| 57 | $\underset{CH_3}{\underset{|}{-C}}=CH$ 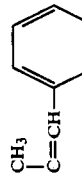 | " | 1.559 | | 7.6(m.1H) 7.3(b.s.5H) 4.9~5.4(m.2H) 2.1(m.6H) 1.4(d.6H) |

-continued

| Compound No. | $R_A$ | $R_B$ | $n_D^{20}$ | Melting point °C | NMR (δppm: CCl$_4$) |
|---|---|---|---|---|---|
| 58 | —(CH$_2$)$_4$CH$_3$ | phenyl | 1.480 | | 7.8~8.2(m.2H) 7.2~7.7(m.3H) 4.7~5.3(m.2H) 2.2(t.2H) 1.0~1.9(m.12H) 0.9(t.3H) |
| 59 | " | 4-CH$_3$-phenyl | 1.481 | | 7.8(d.2H) 7.1(d.2H) 4.7~5.3(m.2H) 2.3(s.3H) 2.0~2.4(t.2H) 1.1~2.0(m.12H) 0.9(t.3H) |
| 60 | " | 4-OCH$_3$-phenyl | 1.492 | | 7.9(d.2H) 6.9(d.2H) 4.8~5.4(m.2H) 3.8(s.3H) 2.0~2.4(t.2H) 1.1~2.0(m.12H) 0.9(t.3H) |
| 61 | " | 4-Cl-phenyl | 1.492 | | 7.7(d.2H) 7.2(d.2H) 4.7~5.3(m.2H) 2.0~2.4(t.2H) 1.1~2.0(m.12H) 0.9(t.3H) |
| 62 | " | 3,4,5-tri-OCH$_3$-phenyl | 1.493 | | 7.2(s.2H) 4.8~5.4(m.2H) 3.8(d.9H) 2.2(t.2H) 1.0~2.0(m.12H) 0.9(t.3H) |
| 63 | " | —CH$_2$CH=CH-phenyl | 1.498 | | 7.0~7.5(m.5H) 6.0~6.6(m.2H) 4.6~5.2(m.2H) 3.2(d.2H) 2.0~2.4(t.2H) 1.1~2.0(m.12H) 0.9(t.3H) |
| 64 | —(CH$_2$)$_9$CH$_3$ | phenyl | 1.477 | | 7.8~8.2(m.2H) 7.2~7.7(m.3H) 4.7~5.4(m.2H) 2.2(t.2H) 1.0~1.9(m.22H) 0.9(t.3H) |
| 65 | " | 4-CH$_3$-phenyl | 1.481 | | 7.75(d.2H) 7.05(d.2H) 4.7~5.3(m.2H) 2.4(s.3H) 2.2(t.2H) 1.1~2.0(m.22H) 0.9(t.3H) |

| Compound No. | $R_A$ | $R_B$ | $n_D^{20}$ | Melting point °C. | NMR (δppm: CCl₄) |
|---|---|---|---|---|---|
| 66 | " | 4-OCH₃-C₆H₄ | 1.488 | | 7.9(d.2H) 6.8(d.2H) 4.8~5.4(m.2H) 3.8(s.3H) 2.2(t.2H) 1.1~2.0(m.22H) 0.9(t.3H) |
| 67 | " | 4-Cl-C₆H₄ | 1.488 | | 7.85(d.2H) 7.3(d.2H) 4.7~5.3(m.2H) 2.2(t.2H) 1.1~2.0(m.22H) 0.9(t.3H) |
| 68 | " | 3,4,5-(OCH₃)₃-C₆H₂ | 1.491 | | 7.15(s.2H) 4.8~5.4(m.2H) 3.8(d.9H) 2.2(t.2H) 1.1~2.0(m.22H) 0.9(t.3H) |
| 69 | " | —CH₂—C₆H₅ | 1.475 | | 7.2(m.5H) 4.6~5.1(m.2H) 3.5(s.2H) 2.1(t.2H) 1.0~1.9(m.22H) 0.9(t.3H) |
| 70 | " | —CH₂CH₂—C₆H₅ | 1.475 | | 7.15(s.5H) 4.7~5.2(m.2H) 2.8(t.2H) 2.7(t.2H) 2.2(t.2H) 1.0~1.9(m.22H) 0.9(t.3H) |
| 71 | " | —CH₂O—C₆H₅ | 1.478 | | 6.7~7.4(m.5H) 4.7~5.2(m.2H) 4.5(s.2H) 2.2(t.2H) 1.0~1.9(m.22H) 0.9(t.3H) |
| 72 | " | —CH(C₂H₅)—C₆H₅ | 1.474 | | 7.2(s.5H) 4.6~5.1(m.2H) 3.3(t.1H) 0.6~2.3(m.28H) |

-continued

| Compound No. | $R_A$ | $R_B$ | $n_D^{20}$ | Melting point °C. | NMR (δppm: CCl₄) |
|---|---|---|---|---|---|
| 73 | —(CH₂)₄CH₃ | —CH= with two phenyl groups (diphenylmethylene, one phenyl attached via CH=) | 1.536 | | 7.65(s.1H) 6.8~7.4(m.10H) 4.7~5.3(m.2H) 2.0~2.5(t.2H) 1.1~2.0(m.12H) 0.9(t.3H) |
| 74 | —(CH₂)₉CH₃ | " | 1.525 | | 7.6(s.1H) 6.7~7.4(m.10H) 4.7~5.1(m.2H) 2.0~2.4(t.2H) 1.1~2.0(m.22H) 0.9(t.3H) |
| 75 | —(CH₂)₄CH₃ | F—C=CH— with phenyl | 1.496 | | 7.1~7.8(m.5H) 6.8(d.1H) 4.7~5.3(m.2H) 2.3(t.2H) 1.1~2.0(m.12H) 0.9(t.3H) |
| 76 | " | CH₃—C=CH— with phenyl | 1.506 | | 7.30(m.5H) 6.15(m.1H) 4.8~5.3(m.2H) 2.56(m.3H) 2.30(t.2H) 1.1~1.9(m.12H) 0.86(t.3H) |
| 77 | —(CH₂)₉CH₃ | CH₃—C=CH— with phenyl | 1.495 | | 7.32(m.5H) 6.10(m.1H) 4.8~5.3(m.2H) 2.58(m.3H) 2.30(t.2H) 1.0~1.9(m.22H) 0.89(t.3H) |
| 78 | —(CH₂)₄CH₃ | —CH= with two phenyl groups | 1.539 | | 7.21(s.10H) 6.30(s.1H) 4.5~5.2(m.2H) 2.28(t.2H) 1.2~1.9(m.6H) 1.08(d.6H) 0.89(t.3H) |
| 79 | —(CH₂)₉CH₃ | —CH= with two phenyl groups | 1.520 | | 7.22(s.10H) 6.30(s.1H) 4.6~5.2(m.2H) 2.30(t.2H) 1.2~1.9(m.16H) 1.10(d.6H) 0.9(t.3H) |

-continued
| Compound No. | $R_A$ | $R_B$ | $n_D^{20}$ | Melting point °C. | NMR (δppm: CCl₄) |
|---|---|---|---|---|---|
| 80 | —(CH₂)₆CH₃ | 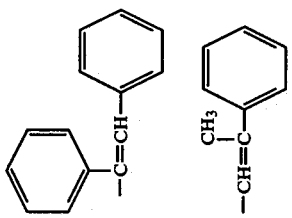 | 1.525 | | 7.7(s.1H) 6.8~7.5(m.10H) 4.7~5.3(m.2H) 2.25(t.2H) 1.0~2.0(m.18H) 0.9(t.3H) |
| 81 | " | 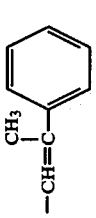 | 1.498 | | 7.0~7.5(m.5H) 6.0(m.1H) 4.6~5.2(m.2H) 2.5(m.3H) 2.2(t.2H) 1.0~2.0(m.18H) 0.9(t.3H) |

The butanediol diester (I) is described below with respect to its antiulcer action and acute toxicity.

(i) Antiulcer action

Wister male rats each weighing about 200 g were given, after fasting for 24 hours, orally 25 mg/kg of indomethacin suspended in 1% aq. solution of sodium carboxymethylcellulose. Five hours later, 1 ml of physiological saline containing 2% brilliant blue was injected intravenously on their tails, and 10 minutes later, they were slaughtered and their stomachs were removed. After fixation by injecting 12 ml of 1% formalin aq. solution, the stomachs were extended on a flat plate and the injured parts on the stomach was measured with slide calipers. The sum of the lengths in mm was regarded as the ulcer index.

The test compound was emulsified or suspended in physiological saline containing one drop of polysolvate 80, and this was given orally or subcutaneously on the back one hour before administration of indomethacin.

The ulcer inhibition ratio was obtained from the following formula.

Inhibition ratio (%) = A/B × 100

A: (ulcer index of control group)—(ulcer index of test group given the test compound)
B: (ulcer index of control group)

The results are shown in Table 2, in which the compound numbers correspond to those in Table 1.

TABLE 2

| Compd. No. | No. of rats | Dosage (mg/kg) | Route | Inhibition ratio (%) |
|---|---|---|---|---|
| 1 | 5 | 200 | Subcutaneously | 92 |
| 2 | " | " | Subcutaneously | 90 |
| 3 | " | " | Subcutaneously | 50 |
| 4 | " | " | Subcutaneously | 74 |
| 6 | " | " | Subcutaneously | 57 |
| 7 | " | " | Subcutaneously | 30 |
| 15 | " | " | Subcutaneously | 47 |
| 16 | " | " | Subcutaneously | 86 |
| 17 | " | " | Subcutaneously | 37 |
| 22 | " | " | Subcutaneously | 91 |
| 24 | " | " | Subcutaneously | 90 |
| 25 | " | " | Subcutaneously | 95 |
| 28 | " | " | Subcutaneously | 62 |
| 31 | " | " | Subcutaneously | 91 |
| 34 | " | " | Subcutaneously | 75 |
| 35 | " | " | Subcutaneously | 77 |
| 37 | " | " | Subcutaneously | 85 |
| 40 | " | " | Subcutaneously | 99 |
| 45 | " | " | Subcutaneously | 84 |
| 46 | " | " | Subcutaneously | 56 |
| 48 | 4 | " | Orally | 84 |
| 48 | 5 | 300 | Subcutaneously | 96 |
| 54 | " | 200 | Subcutaneously | 87 |
| 57 | " | " | Subcutaneously | 80 |
| 60 | " | " | Subcutaneously | 41.4 |
| 62 | " | " | Subcutaneously | 50.0 |
| 64 | " | " | Subcutaneously | 41.3 |
| 68 | " | " | Subcutaneously | 89.3 |
| 70 | " | " | Subcutaneously | 45.9 |
| 71 | " | " | Subcutaneously | 59.2 |

As Table 2 indicates, all of the test compounds are apparently effective in antiulcer action.

(ii) Acute toxicity ddy male mice, arranged in groups each consisting of five mice, were given intraperitoneally 1000 mg/kg of the test compounds Nos. 1–4, 8–10, 14–18, 21, 22, 24, 25, 28, 31, 34, 35, 37, 45, 46, 48, 54, 57, 60, 62, 64, 68, 70, and 71 (as shown in Table 1) dissolved in cotton seed oil. After observation for seven days, all the mice lived without any anomaly. The test compounds were found to have an $LD_{50}$ higher than 1000 mg/kg and a very low toxicity.

The antiulcer drug of this invention can be administered either orally or non-orally in the form of powder, tablets, capsules, granules, solutions, injections (subcutaneous, intramuscular, intravenous), transfusion, and suppositories.

The above-mentioned preparations can be manufactured by the known methods. Powder, tablets, capsules, and granules can be prepared combining butanediol diester with a diluting agent such as starch, lactose, and mannitol; a binder such as sodium carboxymethylcellulose and hydroxypropylcellulose; a disintegrator such as crystalline cellulose calcium carboxymethylcellulose; a lubricant such as talc and magnesium stearate; and a fluidity improving agent such as light silicic anhydride. Solutions and injections can be prepared by dissolving butanediol diester in olive oil or peanut oil, or by dissolving or suspending butanediol diester in water or physiological saline using an anionic surface active agent such as polysolvate 60 and polysolvate 80. Suppositories can be prepared by dispersing butanediol diester in cacao butter or synthetic fats in the conventional manner.

The antiulcer drug thus prepared is administered at the dosage of 0.1 to 1000 mg/kg (orally) and 0.05 to 500 mg/kg (non-orally) once to several times a day for adults.

The invention is illustrated by the following examples.

EXAMPLE 1

Synthesis of Compound No. 22

(1) Dissolve 9 g (0.1 mole) of 2,3-butanediol in 50 ml of ether.
(2) Add 10 ml of pyridine.
(3) With stirring and ice cooling, add dropwise 30 ml of ether solution containing 16.65 g (0.1 mole) of cinnamoyl chloride.
(4) Continue stirring at the cooled temperature for 30 minutes and further continue stirring at room temperature for 4 hours.
(5) Add water and separate the ether layer.
(6) Wash the ether layer with water, 10% hydrochloric acid, water, saturated sodium hydrogenbicarbonate solution, and water in the order listed.
(7) Dry the solution with anhydrous sodium sulfate.
(8) Remove ether by distillation under reduced pressure.
(9) Purify the residue by column chromatography (SiO$_2$) to give 9.4 g of colorless liquid monoester (yield 42.7%).
(10) Dissolve 9.4 g (0.043 mole) of this monoester in 120 ml of ether.
(11) Add 6.8 ml of pyridine.
(12) With stirring and ice cooling, add dropwise 120 ml of ether solution containing 5.75 g (0.043 mole) of caproyl chloride.
(13) Continue stirring at the cooled temperature for 30 minutes and further continue stirring at room temperature for 4 hours.
(14) Add water and separate the ether layer.
(15) Wash the ether layer with water, 10% hydrochloric acid, water, saturated sodium hydrogenbicarbonate solution, and water in the order listed.
(16) Dry the solution with anhydrous sodium sulfate.
(17) Remove ether by distillation under reduced pressure.
(18) Purify the residue by column chromatography (SiO$_2$) to give 9.3 g of colorless liquid which is identified as compound No. 22 in Table 1 (yield 71%).

$n_D^{20}$ 1.514, IR $\nu_{max}^{neat}$ cm$^{-1}$ 1720 (C=O).

EXAMPLE 2

Synthesis of Compound No. 35

(1) With stirring and ice cooling, add dropwise 40 ml of ether solution containing 9 g (0.1 mole) of 2,3-butanediol to 40 ml of ether in which 4 g (0.1 mole) of sodium hydride, is suspended.
(2) Continue stirring at the cooled temperature for 30 minutes and further continue stirring at room temperature for 30 minutes.
(3) With ice cooling again, add dropwise 40 ml of ether solution containing 20.45 g (0.1 mole) of undecanoyl chloride.
(4) Stir at room temperature for 3 hours.
(5) Add water and separate the ether layer.
(6) Carry out the same steps as in Example 1 to give 10.5 g of colorless liquid monoester (yield 40.7%).
(7) Dissolve 10.32 g (0.04 mole) of this monoester in 80 ml of tetrahydrofuran.
(8) Add 6.4 ml of pyridine.
(9) With stirring and ice cooling, add dropwise 80 ml of tetrahydrofuran solution containing 7.86 g (0.04 mole) of p-methoxycinnamoyl chloride.
(10) Continue stirring at the cooled temperature for 30 minutes and further continue stirring at room temperature for 4 hours.
(11) Remove the solvent by distillation under reduced pressure.
(12) Dissolve the residue in chloroform.
(13) Wash the chloroform solution with water, 10% hydrochloric acid, water, saturated sodium hydrogenbicarbonate solution, and water in the order listed.
(14) Dry the solution with anhydrous sodium sulfate.
(15) Remove chloroform by distillation under reduced pressure.
(16) Purify the residue by column chromatography (SiO$_2$) to give 6 g of colorless liquid which is identified as compound No. 35 in Table 1 (yield 35.8%).

$n_D^{20}$ 1.519, IR $\nu_{max}^{neat}$ cm$^{-1}$ 1720 (C=O).

EXAMPLE 3

Synthesis of Compound No. 43

(1) Dissolve 4.5 g (0.05 mole) of 2,3-butanediol in 60 ml of tetrahydrofuran.
(2) Add 10 ml of pyridine.
(3) With stirring and ice cooling, add dropwise 60 ml of tetrahydrofuran solution containing 19.15 g (0.1 mole) of α-cyanocinnamoyl chloride.
(4) Continue stirring at the cooled temperature for 30 minutes and further continue stirring at room temperature for 4 hours.
(5) Remove the solvent by distillation under reduced pressure.
(6) Dissolve the residue in chloroform.
(7) Wash the chloroform solution with water, 10% hydrochloric acid, water, saturated sodium hydrogenbicarbonate solution, and water in the order listed.
(8) Dry the solution with anhydrous sodium sulfate.
(9) Remove chloroform by distillation under reduced pressure.
(10) Recrystallize the residue from benzene to give 12.4 g of light yellow needle crystal, which is identified as compound No. 43 in Table 1 (yield 62%).

Melting point: 177° to 180° C.
IR $\nu_{max}^{KBr}$ cm$^{-1}$ 1720 (C=O).

EXAMPLE 4

Synthesis of Compound 60

(1) With stirring and ice cooling, add 40 ml of ether solution containing 6.3 g (0.07 mole) of 2,3-butanediol to 40 ml of ether in which 3.0 g (0.075 mole) of sodium hydride is suspended.
(2) Continue stirring at the cooled temperature for 30 minutes and further continue stirring at room temperature for 30 minutes.

(3) With ice cooling again, add dropwise 40 ml of ether solution containing 11.9 g (0.07 mole) of p-anisoyl chloride.
(4) Stir at room temperature for 3 hours.
(5) Add water and separate the ether layer.
(6) Wash the ether layer with water, 10% hydrochloric acid, water, saturated sodium hydrogencarbonate solution, and water in the order listed.
(7) Dry the ether layer with anhydrous sodium sulfate.
(8) Remove ether by distillation under reduced pressure.
(9) Purify the residue by column chromatography (SiO$_2$) to give 6.8 g of colorless liquid monoester (yield 43.4%).
(10) Dissolve 2.02 g (0.009 mole) of this monoester in 20 ml of ether.
(11) Add 2 ml of pyridine.
(12) With stirring and ice cooling, add dropwise 20 ml of ether solution containing 1.22 g (0.009 mole) of n-caproyl chloride.
(13) Continue stirring at the cooled temperature for 30 minutes and further continue stirring at room temperature for 3 hours.
(14) Add water and separate the ether layer.
(15) Wash the ether layer with water, 10% hydrochloric acid, water, saturated sodium hydrogenbicarbonate solution, and water in the order listed.
(16) Dry the solution with anhydrous sodium sulfate.
(17) Remove ether by distillation under reduced pressure.
(18) Purify the residue by column chromatography (SiO$_2$) to give 2.7 g of colorless liquid which is identified as compound No. 60 in Table 1 (yield 93.2%).

$n_D^{20}$ 1.492, IR $\nu_{max}^{neat}$ cm$^{-1}$ 1720 C=O).

EXAMPLE 5

Synthesis of Compound 68

(1) With stirring and ice cooling, and 20 ml of ether solution containing 2.7 g (0.03 mole) of 2,3-butanediol to 40 ml of tetrahydrofuran in which 1.2 g (0.03 mole) of sodium hydride is suspended.
(2) Continue stirring at the cooled temperature for 30 minutes and further continue stirring at room temperature for 30 minutes.
(3) With ice cooling again, add dropwise 40 ml of tetrahydrofuran solution containing 6.92 g (0.03 mole) of 3,4,5-trimethoxybenzoyl chloride.
(4) Stir at room temperature for 5 hours.
(5) Remove the solvent by distillation under reduced pressure.
(6) Dissolve the residue in chloroform.
(7) Wash the chloroform layer with water, 10% hydrochloric acid, water, saturated sodium hydrogenbicarbonate solution, and water in the order listed.
(8) Dry the chloroform layer with anhydrous sodium sulfate.
(9) Remove chloroform by distillation under reduced pressure.
(10) Purify the residue by column chromatography (SiO$_2$) to give 3.66 g of colorless liquid monoester (yield 43%).
(11) Dissolve 2.84 g (0.01 mole) of this monoester in 20 ml of ether.
(12) Add 2 ml of pyridine.
(13) With ice cooling, add dropwise 20 ml of ether solution containing 2.05 g (0.01 mole) of undecanoyl chloride.
(14) Continue stirring at the cooled temperature for 30 minutes and further continue stirring at room temperature for 3 hours.
(15) Add water and separate the ether layer.
(16) Wash the ether layer with water, 10% hydrochloric acid, water, saturated sodium hydrogenbicarbonate solution, and water in the order listed.
(17) Dry the ether layer with anhydrous sodium sulfate.
(18) Remove ether by distillation under reduced pressure.
(19) Purify the residue by column chromatography (SiO$_2$) to give 2.04 g of colorless liquid which is identified as compound No. 68 in Table 1 (yield 50%).

$n_D^{20}$ 1.491, IR $\nu_{max}^{neat}$ cm$^{-1}$ 1720 (C=O).

EXAMPLE 6

Synthesis of Compound No. 70

(1) Dissolve 9 g (0.1 mole) of 2,3-butanediol in 50 ml of ether.
(2) Add 10 ml of pyridine.
(3) With stirring and ice cooling, add dropwise 75 ml of ether solution containing 20.5 g (0.1 mole) of undecanoyl chloride.
(4) Continue stirring at the cooled temperature for 30 minutes and further continue stirring at room temperature for 4 hours.
(5) Add water and separate the ether layer.
(6) Carry out the treatment as in Example 4 to give 13.2 g of colorless liquid monoester (yield 51%).
(7) Dissolve 12.9 g (0.05 mole) of this monoester in 100 ml of ether.
(8) Add 10 ml of pyridine.
(9) With stirring and ice cooling, add dropwise 100 ml of ether solution containing 8.43 g (0.05 mole) of phenylpropionyl chloride.
(10) Continue stirring at the cooled temperature for 30 minutes and further continue stirring at room temperature for 3 hours.
(11) Add water and separate the ether layer.
(12) Wash the ether layer with water, 10% hydrochloric acid, water, saturated sodium hydrogenbicarbonate solution, and water in the order listed.
(13) Dry the solution with anhydrous sodium sulfate.
(14) Remove ether by distillation under reduced pressure.
(15) Purify the residue by column chromatography (SiO$_2$) to give 16.2 g of colorless liquid which is identified as compound No. 70 in Table 1 (yield 85.3%).

$n_D^{20}$ 1.475, IR $\nu_{max}^{neat}$ cm$^{-1}$ 1720 (C=O).

EXAMPLE 7

Preparation of Tablet

A tablet of the following composition was prepared according to the conventional manner.

| | |
|---|---|
| Butanediol diester (Compound No. 1 in Table 1) | 100 mg |
| Light silicic anhydride | 100 mg |
| Crystalline cellulose | 50 mg |
| Hydroxypropyl cellulose | 10 mg |
| Calcium carboxymethylcellulose | 25 mg |
| Talc | 4 mg |

EXAMPLE 8

Preparation of Granules

Granules of the following composition were prepared according to the conventional manner.

| | |
|---|---|
| Butanediol diester (Compound No. 1 in Table 1) | 100 mg |
| Light silicic anhydride | 100 mg |
| Mannitol | 650 mg |
| Starch | 135 mg |
| Polyvinyl pyrrolidone | 15 mg |
| Total | 1000 mg |

EXAMPLE 9

Preparation of Injection

An oil injection of the following composition were prepared according to the conventional manner.

| | |
|---|---|
| Butanediol diester (Compound No. 2 in Table 1) | 100 mg |
| Peanut oil | 1900 mg |
| Total | 2000 mg |

EXAMPLE 10

Preparation of Suppository

A suppository of the following composition were prepared according to the conventional manner.

| | |
|---|---|
| Butanediol diester (Compound No. 2 in Table 1) | 100 mg |
| Cacao butter | 1000 mg |
| Total | 1100 mg |

EXAMPLE 11

Preparation of Tablet

A tablet of the following composition was prepared according to the conventional manner.

| | |
|---|---|
| Butanediol diester (Compound No. 31 in Table 1) | 100 mg |
| Light silicic anhydride | 100 mg |
| Crystalline cellulose | 50 mg |
| Hydroxypropyl cellulose | 10 mg |
| Calcium carboxymethylcellulose | 25 mg |
| Talc | 4 mg |
| Magnesium stearate | 2 mg |
| Lactose | An amount sufficient to bring the final weight to 350 mg |

EXAMPLE 12

Preparation of Granules

Granules of the following composition were prepared according to the conventional manner.

| | |
|---|---|
| Butanediol diester (Compound No. 25 in Table 1) | 100 mg |
| Light silicic anhydride | 100 mg |
| Mannitol | 650 mg |
| Starch | 135 mg |
| Polyvinyl pyrrolidone | 15 mg |
| Total | 1000 mg |

EXAMPLE 13

Preparation of Injection

An oil injection of the following composition were prepared according to the conventional manner.

| | |
|---|---|
| Butanediol diester (Compound No. 31 in Table 1) | 100 mg |
| Peanut oil | 1900 mg |
| Total | 2000 mg |

EXAMPLE 14

Preparation of Suppository

A suppository of the following composition were prepared according to the conventional manner.

| | |
|---|---|
| Butanediol diester (Compound No. 40 in Table 1) | 100 mg |
| Cacao butter | 1000 mg |
| Total | 1100 mg |

EXAMPLE 15

Preparation of Tablet

A tablet of the following composition was prepared according to the conventional manner.

| | |
|---|---|
| Butanediol diester (Compound No. 68 in Table 1) | 100 mg |
| Light silicic anhydride | 100 mg |
| Crystalline cellulose | 50 mg |
| Hydroxypropyl cellulose | 10 mg |
| Calcium carboxymethylcellulose | 25 mg |
| Talc | 4 mg |
| Magnesium stearate | 2 mg |
| Lactose | An amount sufficient to bring the final weight to 350 mg |

EXAMPLE 16

Preparation of Granules

Granules of the following composition were prepared according to the conventional manner.

| | |
|---|---|
| Butanediol diester (Compound No. 62 in Table 1) | 100 mg |
| Light silicic anhydride | 100 mg |
| Mannitol | 650 mg |
| Starch | 135 mg |
| Polyvinyl pyrrolidone | 15 mg |
| Total | 1000 mg |

-continued (from previous)

| | |
|---|---|
| Magnesium stearate | 2 mg |
| Lactose | An amount sufficient to bring the final weight to 350 mg |

EXAMPLE 17

Preparation of Injection

An oil injection of the following composition were prepared according to the conventional manner.

| | |
|---|---|
| Butanediol diester | 100 mg |
| (Compound No. 71 in Table 1) | |
| Peanut oil | 1900 mg |
| Total | 2000 mg |

EXAMPLE 18

Preparation of Suppository

A suppository of the following composition were prepared according to the conventional manner.

| | |
|---|---|
| Butanediol diester | 100 mg |
| (Compound No. 68 in Table 1) | |
| Cacao butter | 1000 mg |
| Total | 1100 mg |

What is claimed is:

1. An antiulcer composition comprising, as an active ingredient, an antiulcer effective amount of a 2,3-butanediol diester represented by the formula (I):

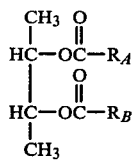

where $R_A$ is a saturated alkyl group which may have a branched chain, or a group represented by the formula

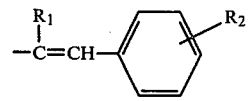

where
$R_1$ is hydrogen, cyano or lower alkyl, and
$R_2$ is hydrogen, halogen, lower alkyl, lower alkyloxy or lower acyloxy;
$R_B$ is a saturated alkyl group which may have a branched chain, phenyl group which may be substituted with lower alkyl, lower alkoxy or halogen, phenyl alkyl, phenyl propenyl, phenyloxy alkyl or a group represented by the formula

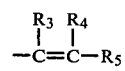

where
$R_3$ is hydrogen, halogen, cyano, lower alkyl or phenyl,
$R_4$ is hydrogen, lower alkyl or phenyl, and
$R_5$ is phenyl which may be substituted with lower alkyl, lower alkoxy, acyloxy or halogen; and
a pharmaceutically acceptable compound selected from the group consisting of a diluent, a binder, a disintegrator, a lubricant, a fluidity improving agent, olive oil, peanut oil, water, physiological saline, cacao butter and synthetic fat.

2. The antiulcer composition according to claim 1, wherein the diluent is starch, lactose or mannitol.

3. The antiulcer composition according to claim 1, wherein the binder is sodium carboxymethylcellulose or hydroxypropylcellulose.

4. The antiulcer composition according to claim 1, wherein the disintegrator is crystalline cellulose calcium carboxymethylcellulose.

5. The antiulcer composition according to claim 1, wherein the lubricant is talc or magnesium stearate.

6. The antiulcer composition according to claim 1, wherein the fluidity improving agent is light silicic anhydride.

7. The antiulcer composition according to claim 1, in the form of powder, tablets, capsules, granules, solutions or suppositories.

8. The antiulcer composition according to claim 1 in a form for oral administration.

* * * * *

UNITED STATES PATENT AND TRADEMARK OFFICE
CERTIFICATE OF CORRECTION

PATENT NO. : 4,469,704
DATED : September 4, 1984
INVENTOR(S) : SUSUMU SATOH ET AL It is certified that error appears in the above-identified patent and that said Letters Patent is hereby corrected as shown below:

In the Abstract, second line under the Figure, delete "phenyl".

Col. 1, line 64, delete ".".

Col. 2, third line of the first Figure, change "HC O$\overset{\overset{O}{\|}}{C}$-R$_{B'}$," to -- HC — O$\overset{\overset{O}{\|}}{C}$-R$_{B'}$ --.

Col. 4, in the Figure, add a -- $\longrightarrow$ -- immediately after "2.R$_A$COOH".

Col. 17, in the Table under the heading "R$_A$" for compound 75, change "-(CH$_2$)$_4$CH$_4$" to -- -(CH$_2$)$_4$CH$_3$ --.

Col. 22, line 63, between "cellulose" and "calcium" add --and--.

UNITED STATES PATENT AND TRADEMARK OFFICE
CERTIFICATE OF CORRECTION

PATENT NO. : 4,469,704

DATED : September 4, 1984

INVENTOR(S) : Susumu Satoh et al

It is certified that error appears in the above-identified patent and that said Letters Patent is hereby corrected as shown below:

Col. 25, line 41, change "and" (second occurrence) to --add--.

Signed and Sealed this

Fifteenth Day of October 1985

[SEAL]

Attest:

DONALD J. QUIGG

Attesting Officer

Commissioner of Patents and Trademarks—Designate